United States Patent [19]

Kohayakawa

[11] Patent Number: 5,420,650

[45] Date of Patent: May 30, 1995

[54] EYE EXAMINING APPARATUS INCLUDING AN EYE REFRACTION MEASURING SYSTEM AND EYE FUNDUS EXAMINING SYSTEM

[75] Inventor: Yoshimi Kohayakawa, Yokohama, Japan

[73] Assignee: Canon Kabushiki Kaisha, Japan

[21] Appl. No.: 95,219

[22] Filed: Jul. 23, 1993

[30] Foreign Application Priority Data

Jul. 30, 1992 [JP] Japan .................. 4-222222

[51] Int. Cl.$^6$ ................................ A61B 3/10
[52] U.S. Cl. .................... 351/206; 351/211; 351/214; 351/221
[58] Field of Search ........... 351/200, 205, 206, 211, 351/214, 221, 243

[56] References Cited

U.S. PATENT DOCUMENTS

| | | | |
|---|---|---|---|
| 3,614,214 | 10/1971 | Cornsweet | 351/211 |
| 4,372,655 | 2/1983 | Matsumura et al. | 351/206 |
| 4,609,287 | 9/1986 | Kohayakawa | 356/124 |
| 4,755,041 | 7/1988 | Ishikawa et al. | 351/211 |
| 4,820,037 | 4/1989 | Kohayakawa et al. | 351/211 |
| 4,825,873 | 5/1989 | Kohayakawa | 128/648 |
| 4,826,315 | 5/1989 | Kohayakawa | 356/125 |
| 4,859,051 | 8/1989 | Fukuma et al. | 351/211 |
| 5,031,623 | 7/1991 | Kohayakawa et al. | 128/648 |
| 5,037,194 | 8/1991 | Kohayakawa et al. | 351/224 |
| 5,144,346 | 9/1992 | Nakamura et al. | 351/208 |
| 5,231,430 | 7/1993 | Kohayakawa et al. | 351/243 |
| 5,237,351 | 8/1993 | Kohayakawa et al. | 351/243 |
| 5,270,749 | 12/1993 | Okumura | 351/211 |

*Primary Examiner*—William L. Sikes
*Assistant Examiner*—David R. Parsons
*Attorney, Agent, or Firm*—Fitzpatrick, Cella, Harper & Scinto

[57] ABSTRACT

The present invention relates to an eye examining apparatus used in ophthalmic clinics. In an eye refractometer provided with a light beam separating member for separating an eye fundus illuminating light beam and an imaging light beam through an objective lens in a position conjugate with the pupil of an eye to be examined, an eye refraction measuring light beam is projected to the fundus of the eye to be examined through an optical passage dividing member arranged between the aforesaid objective lens and the aforesaid light beam separating member in order to obtain the refractive value of the eye to be examined by receiving the aforesaid measuring light beam including at least three meridians using a photoelectric sensor.

10 Claims, 5 Drawing Sheets

EYE EXAMINING APPARATUS INCLUDING AN EYE REFRACTION MEASURING SYSTEM AND EYE FUNDUS EXAMINING SYSTEM

BACKGROUND OF THE INVENTION

1. Field of the Invention

The present invention relates to an eye examining apparatus used at an ophthalmic clinic and an opticians' store.

2. Related Background Art

When photographing an eye fundus and refracting an eye at the same time, it has hitherto been required to install two apparatuses, an eye fundus camera and an eye refractometer. As a result, more space is needed for the installation, leading to an increased expense. It is also troublesome that an examinee should move in a distance between the two apparatuses.

SUMMARY OF THE INVENTION

The present invention is designed with a view to overcoming the above-mentioned problems. It is a prime object of the invention to provide an eye refractometer capable of refracting an eye and photographing an eye fundus by use of a single apparatus.

The above-mentioned and other objects, features, and advantages of the present invention will become more apparent by reference to the detailed description of the embodiments set forth below.

DETAILED DESCRIPTION OF THE PREFERRED EMBODIMENTS

In order to achieve the above-mentioned and other objects, each of the following embodiments is an eye refractometer provided with a light beam separating member which separately provides an eye fundus illuminating light flux and a photographing light flux through an objective lens in a position conjugate with the pupil of an eye to be examined, wherein an eye refraction measuring light flux is projected to the fundus of the eye to be examined through an optical passage dividing member which is arranged between the aforesaid objective lens and the light beam separating member so that the refractive value of the eye to be examined is obtained by receiving the aforesaid measuring light beam including at least three meridians by means of a photoelectric sensor.

The embodiments will be described in detail in conjunction with the accompanying drawings as follows.

Figure 1:
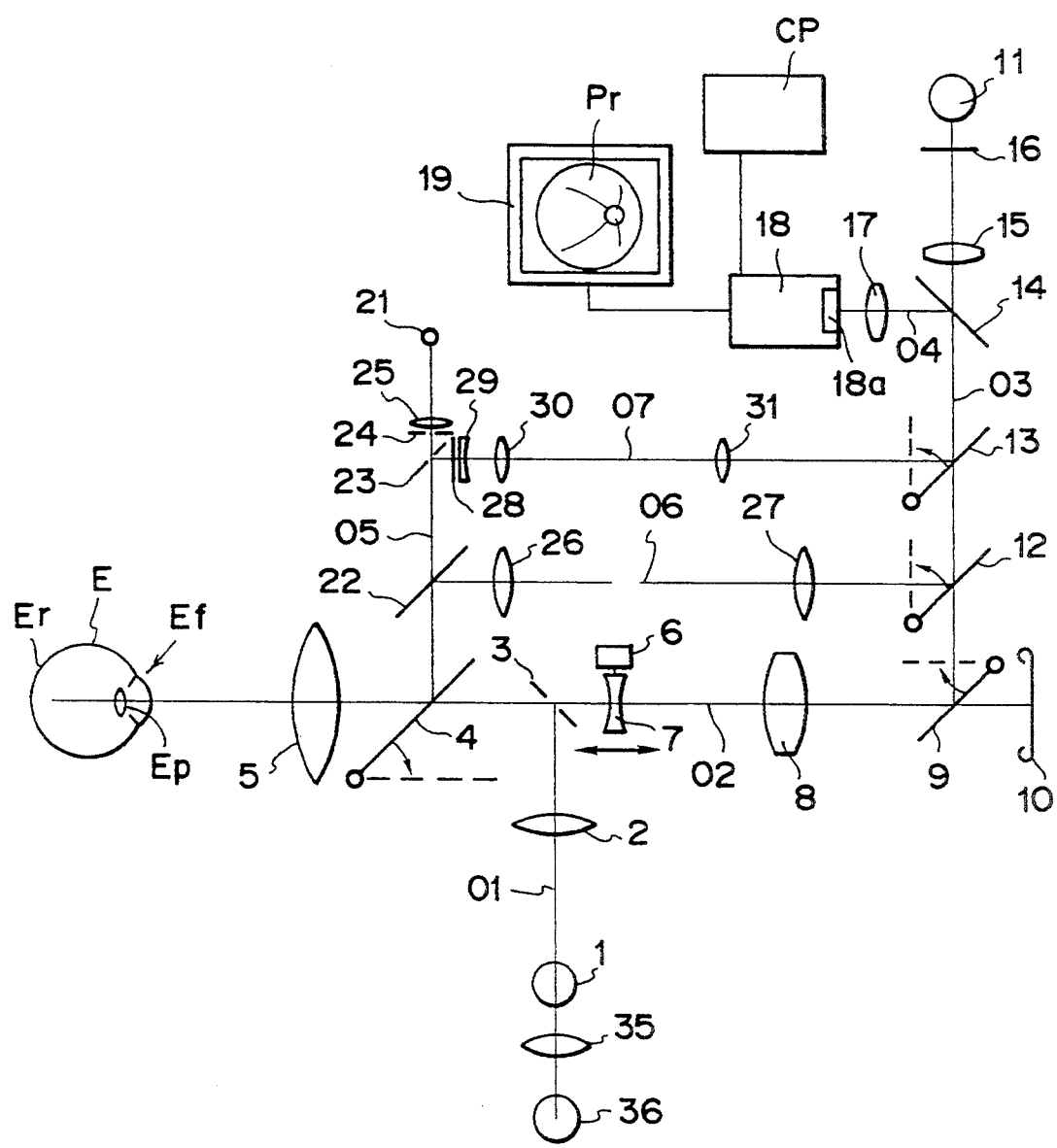
FIG. 1 is a view schematically showing the structure of a first embodiment.

FIG. 1 is a view showing schematically the structure of an apparatus provided with the functions of an eye refractometer and an eye fundus camera according to a first embodiment. On an optical passage 01 from a light source 36 emitting an infrared light to an eye to be examined E, there are arranged lenses 35 and 2, a holed mirror 3 provided at a position conjugate with the pupil of an eye to be examined, a movable dichroic mirror 4 which reflects the infrared light but transmits the visible light, and an objective lens 5. On an optical passage 02 behind the holed mirror 3, there are arranged a focus lens 7 driven along the optical axis by driving means 6, a lens 8, a movable mirror 9, and a film 10. On an optical passage 03 from the movable mirror 9 to a light source 11, there are arranged the movable dichroic mirrors 12 and 13 which reflect the infrared light but transmit the visible light, a dichroic mirror 14 which transmits the visible light but reflects the infrared light, a lens 15, and a refraction target 16. On an optical passage 04 in the reflecting direction of the dichroic mirror 14, a lens 17 and a television camera 18 having an image sensor 18a are arranged. To the output of the television camera 18, a television monitor 19 is connected.

Figure 2:
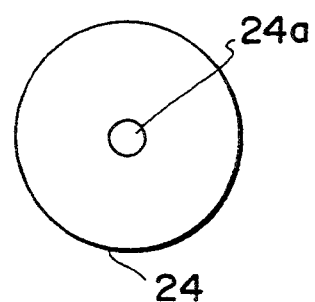
FIG. 2 is a front view illustrating a central aperture stop.
Figure 3:
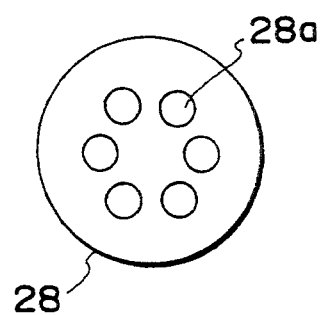
FIG. 3 is a front view illustrating a six-hole aperture stop.
Figure 4:
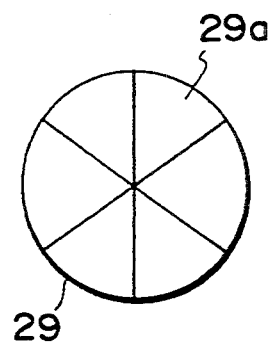
FIG. 4 is a front view illustrating a separate prism.

Also, on an optical passage 05 from the movable dichroic mirror 4 to a measurement light source 21 which emits the infrared light, there are arranged a dichroic mirror 22, a holed mirror 23, a central aperture stop 24 conjugate with a pupil Ep, which is provided with an aperture 24a shown in FIG. 2, and a lens 25. On an optical passage 06 from the dichroic mirror 22 to the movable dichroic mirror 12, lenses 26 and 27 are arranged. On an optical passage 07 from the holed mirror 23 to the movable dichroic mirror 13, are a six-hole aperture stop 28 having six apertures 28a shown in FIG. 3, a separate prism 29 comprising six wedge prisms 29a shown in FIG. 4, and lenses 30 and 31. The six-hole aperture stop 28 is in a position conjugate with the pupil Ep of the eye to be examined E. The central aperture stop 24 and the six-hole aperture stop 28 are arranged so that the light flux projected to the eye fundus and the light flux reflected by the eye fundus are positionally separated on the pupil Ep of the eye to be examined.

Figure 5:
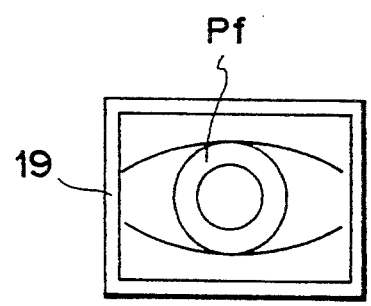
FIG. 5 is a view illustrating the image of an anterior eye part shown on a television monitor.

When the anterior eye part is observed, the movable dichroic mirror 4, movable mirror 9, and movable dichroic mirror 12 are inserted in the positions represented by solid lines. The movable dichroic mirror 13 is retracted from the optical passage 03 as indicated by a dotted line. The reflected light beam from the anterior eye part Ef illuminated by an infrared light which is not shown, is reflected by the movable dichroic mirror 12 after passing the objective lens 5, movable dichroic mirror 4, dichroic mirror 22, lens 26, and lens 27, and is further reflected by the dichroic mirror 14 to form an image on the image sensor 18a of the television camera 18 through the lens 17. Thus, the anterior eye part Pf is displayed on the television monitor 19 as shown in FIG. 5.

When the eye fundus is observed, the examiner first adjusts the position of the apparatus while watching the image of the anterior eye part Pf on the television monitor 19, and shift the movable dichroic mirrors 4 and 12 to the positions indicated by dotted lines after the adjustment. The light beam from the light source 36 passes the lenses 35 and 2 and illuminates the eye fundus Er through the objective lens 5 after being reflected by the holed mirror 3. This reflected light beam advances on the same passages to the right-hand side and passes the holed mirror 3, focus lens 7, and lens 8, thus being reflected by the movable mirror 9 and further by the dichroic mirror 14 to form an image on the image sensor 18a of the television camera 18 through the lens 17. Hence, the image of the eye fundus Pr is displayed on the television monitor 19.

When the eye fundus is photographed, the examiner drives the focus lens 7 for focusing by use of the driving means 6 while watching the image of the eye fundus Er on the television monitor 19. To photograph the image of the eye fundus Pr on the film 10, a strobe light source 1 is lit after retracting the movable mirror 9 from the optical passage 02.

Figure 6:
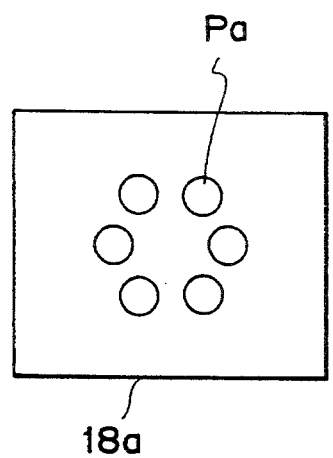
FIG. 6 is a view illustrating the image of measuring luminous flux on an image sensor.

When refracting the eye, the movable dichroic mirrors 4, 12 and 13, and the movable mirror 9 are set as illustrated by solid lines in FIG. 1. The necessary positioning of the apparatus is done while observing the eye anterior part through the optical path 06. The refraction target is presented at the proper diopter by adjusting the position of the focus lens 7 through the optical paths 03 and 02. Then the infrared measuring light source 21 projects a spot flux of the eye fundus Er and the reflected light passes the optical paths 05, 07, 03 and 04 to project six light spots on the image sensor 18a as illustrated in FIG. 6. The positions of these six light spots are analyzed by a computer CP to obtain the value of the eye refraction including astigmatism.

In this respect, the movable dichroic mirror 13 is designed so that the mirror 13 transmits the infrared light for the anterior eye observation, but reflects the infrared light from the light source 21. Therefore, even after the movable dichroic mirror 13 is inserted, the image of the anterior eye part can be observed on the monitor 19. The movable dichroic mirror 12 is instantaneously shifted to the position indicated by the dotted line for the required measurement and then, the reflected light beam from the anterior eye part Ef is blocked in reaching the image sensor 18a of the television camera 18. Thus, it does not hinder the positional analysis to be executed by the above-mentioned computer CP.

Figure 7:
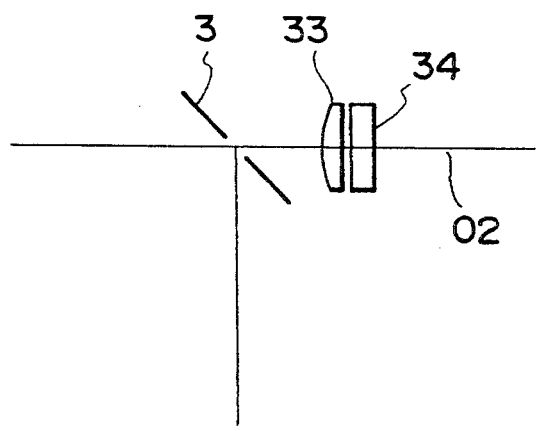
FIG. 7 is a view schematically showing the structure of a variation of the imaging optical system.

In the present embodiment, when the value of the eye refraction is measured before the eye fundus is photographed, it is possible to drive the focus lens 7 to be at the focusing position for the eye fundus photographing in advance by the computer CP controlling the driving means 6 utilizing the data thus obtained in the eye refraction measurement. Also, it is possible to continuously execute the measurement and photographing. Further, in the eye fundus camera provided with the cross cylinders 33 and 34 which are arranged on the optical passage 02 behind the holed mirror 3 as shown in FIG. 7, it is possible to photograph the eye fundus of the eye E after correcting the astigmatism by the cross cylinders 33 and 34 driven by utilizing the data obtained in the eye refraction measurement.

In the present embodiment, there is provided between the objective lens 5 and the holed mirror 3, the movable dichroic mirror 4 which serves as an optical passage dividing means for introducing the optical passage for the eye refraction measuring system into the optical passage 02 for the eye fundus photographing system. The fundus illuminating optical passage 01 and photographing optical passage 02 for the usual photographing are divided by the use of means such as the holed mirror 3 conjugate to the pupil Ep for separating the incident light beam and exit light beam. On the other hand, the eye refraction measuring system is usually provided with stop means for regulating the light beam for eye refraction measurement which is usually in a position conjugate with the pupil. In the present embodiment, the optical passage dividing means is arranged between the objective lens and the holed mirror 3. Accordingly, the positions conjugate with the pupil are formed in the photographing passage and the eye refraction measuring passage, respectively. Thus, there is no interference by each of the optical systems, allowing a single apparatus having two kinds of capabilities.

Figure 8:
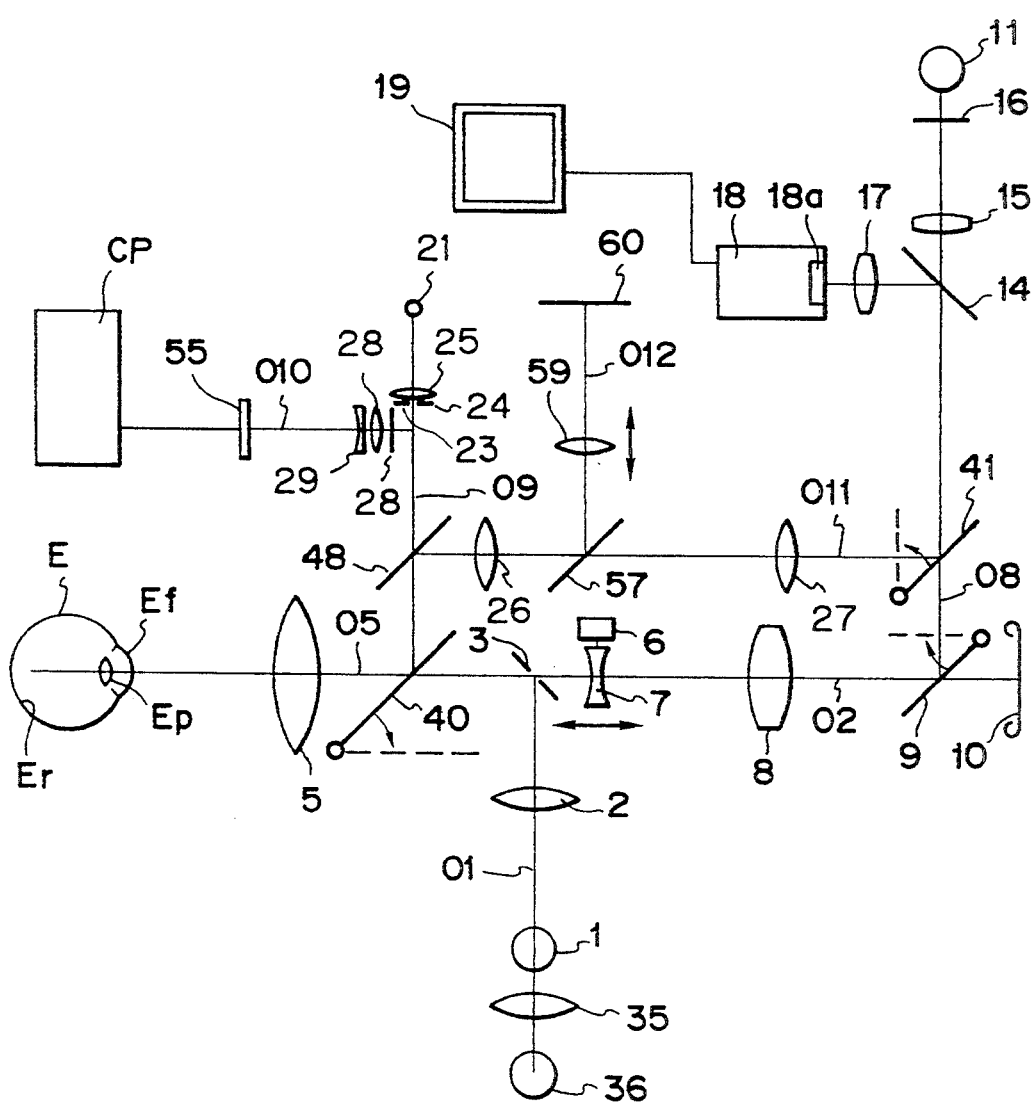
FIG. 8 is a view schematically showing a second embodiment according to the present invention.

FIG. 8 shows a second embodiment according to the present invention, which is the same as the first embodiment with the exception that the movable dichroic mirror 4 in FIG. 1 is replaced by a movable mirror 40. Also, the dioptric induction system by the use of the light source 11 and the television image sensing system are the same as those shown in FIG. 1. On the optical passage 08 in the reflective direction of the movable mirror 9, a movable mirror 41, dichroic mirror 14, lens 15, dioptric induction target 16, and light source 11 are arranged. On the optical passage 09 from the movable mirror 40 to a measuring light source 47, a dichroic mirror 48, holed mirror 49, central aperture stop 50 conjugate with the pupil of an eye to be examined, and lens 51 are arranged. On the optical passage 010 in the reflective direction of the holed mirror 49, a six-hole aperture stop 52 conjugate with the pupil of an eye to be examined, lens 53, separate prism 54, and two-dimensional CCD 55 are arranged. Also, on the optical passage 011 from the dichroic mirror 48 to the movable mirror 41, a lens 56, the dichroic mirror 57 which reflects any visible light, but transmits the infrared light, and a lens 58 are arranged. On the optical passage 012 in the reflective direction of the dichroic mirror 57, the movable lens 59 which can be shifted along the optical axis, and a dioptric induction target 60 are arranged.

When the anterior eye part is observed, the movable mirrors 40 and 41 are in the positions indicated by solid lines. The reflected light beam from the anterior eye part Ef is reflected by the movable mirror 40 and the dichroic mirror 48 after passing the objective lens 5, and is reflected by the movable mirror 41 and dichroic mirror 14 after passing the lens 56, dichroic mirror 57, and lens 58 to form the image of the anterior eye on the lens 17, and the photographing element 18a of the television camera 18 through the lens 17, which is screened on the television monitor.

When the eye fundus is observed, the movable mirrors 40 and 41 are shifted to the position indicated by the dotted lines while the movable mirror 9 is in the position indicated by the solid line. The light beam from the light source 36 is reflected by the holed mirror 3 to irradiate the eye fundus Er through the objective lens 5. This reflected light beam is reflected by the movable mirror 9 and dichroic mirror 14 after passing the objective lens 5, holed mirror 3, focus lens 7, and lens 8 to form the image of the eye fundus on the photographing element 18a of the television camera 18 through the lens 17. When the eye fundus is photographed, the strobe light source 1 is allowed to emit light and the movable mirror 9 is shifted to the position indicated by the dotted line. Hence, the eye fundus image is sensed on the film 10.

When the eye refraction is measured, the movable mirror 40 is inserted to the optical passage 01. The light beam from the dioptric induction target 60 is reflected by the dichroic mirror 57 through the movable mirror 59, and is reflected by the dichroic mirror 48 and movable mirror 40 through the lens 56, thus arriving at the eye fundus Er through the objective lens 5. The apparent diopter according to this dioptric induction target 60 is varied by the movable lens 59 to execute the dioptric induction of the eye to be examined E.

The infrared light beam from the measuring light source 47 is reflected by the movable mirror 40 after passing the lens 51, central aperture stop 50, holed mirror 49, and dichroic mirror 48, and is projected as a state of a point on the eye fundus Er through the objective lens 5. Returning on the same optical passage, this reflected light is reflected by the holed mirror 49 to pass the six-hole aperture stop 52, lens 53, and separate prism 54, thus being received as measuring luminous flux Pa on the two-dimensional CCD 55 as shown in FIG. 6. The position of this light beam Pa is analyzed by a computer CP to obtain the value of the eye refraction including any astigmatism. Here, in the present embodiment, the measuring luminous flux is received by the two-dimensional CCD 55, but the present invention is not necessarily limited thereto.

When the fundus image is recorded by the image sensor 18a with the strobe 1, the film 10 is not necessary.

When the anterior of the eye E is observed through the optical path 02, the lens 27 and the movable mirror 41 are not necessary. To do this, an extra lens must be inserted between the holed mirror 3 and the movable mirror 40 which is replaced by a movable dichroic mirror transmitting the light illuminating the anterior of the eye.

As described above, a refraction measurement optical passage and an anterior eye observation optical passage are guided through an optical passage dividing member arranged between an objective lens and the light beam separation element of an eye fundus photographing system, hence making it possible to implement the provision of an instrument having both functions of eye fundus photographing and refraction.

What is claimed is:

1. An ophthalmic apparatus comprising:
    an objective lens arranged in a position opposite to an eye to be examined;
    a light beam separating element, located at a position conjugate with the pupil of an eye to be examined, for separating a first optical path and a second optical path from the eye to be examined;
    an eye fundus illuminating system for illuminating the fundus of an eye to be examined from the first optical path through said light beam separating element and said objective lens;
    an eye fundus imaging system for imaging the eye fundus, said eye fundus imaging system guiding an imaging light beam from the eye fundus illuminated by said eye fundus illuminating system to the second optical path through said objective lens and said light beam separating element;
    an eye refraction measuring system for projecting eye refraction measuring light to the fundus of an eye to be examined, and for measuring refractive information of an eye to be examined by detecting eye refraction measuring light reflected from the eye fundus; and
    an optical path dividing member, arranged between said objective lens and said light beam separating element for dividing an optical path of said eye refraction measuring system and an optical path of said eye fundus illuminating system and said eye fundus imaging system.

2. An apparatus according to claim 1, further comprising an anterior eye part observing system for allowing observation of the anterior eye part of an eye to be examined through said objective lens.

3. An apparatus according to claim 1, wherein
    said eye fundus imaging system photographs the image of an eye fundus on a film.

4. An apparatus according to claim 1, wherein said eye refraction measuring system is provided with a multi-apertured stop for transmitting the eye refraction measuring light reflected from the eye fundus through said multi-apertured stop and for producing a plurality of light beams from the transmitted light so that the eye refractive information of the eye to be examined is measured according to incident positions of the plurality of light beams upon a photodetecting element.

5. An apparatus according to claim 1, further comprising an induction target system for inducing the diopter of an eye to be examined when said eye refraction measuring system executes a measurement.

6. An apparatus according to claim 5, wherein
    a movable lens of said induction target system and a focus lens of said eye fundus imaging system are used together.

7. An apparatus according to claim 1, wherein said light beam separating element comprises a mirror having an aperture for transmitting light.

8. An ophthalmic apparatus comprising:
    an objective lens arranged in a position opposite to an eye to be examined;
    a light beam separating element, located at a position conjugate with the pupil of an eye to be examined, for separating a first optical path and a second optical path from the eye to be examined;
    an eye fundus illuminating system for illuminating the fundus of an eye to be examined from the first optical path through said light beam separating element and said objective lens;
    an eye fundus imaging system for imaging the eye fundus, said eye fundus imaging system guiding an imaging light beam from the eye fundus illuminated by said eye fundus illuminating system to the second optical path through said objective lens and said light beam separating element;
    an eye refraction measuring system for projecting eye refraction measuring light to the fundus of an eye to be examined, and for measuring refractive information of an eye to be examined by detecting eye refraction measuring light reflected from the eye fundus;
    an optical path dividing member, arranged between said objective lens and said light beam separating element for dividing an optical path of said eye refraction measuring system and an optical path of said eye fundus illuminating system and said eye fundus imaging system;
    an anterior eye part observing system for allowing observation of the anterior eye part of an eye to be examined through said objective lens; and
    a photodetecting element for recording light from said eye refraction measuring system and said anterior eye part observing system.

9. An ophthalmic apparatus comprising:
    an objective lens arranged in a position opposite to an eye to be examined;
    a light beam separating element, located at a position conjugate with the pupil of an eye to be examined, for separating a first optical path and a second optical path from the eye to be examined;

an eye fundus illuminating system for illuminating the fundus of an eye to be examined from the first optical path through said light beam separating element and said objective lens;

an eye fundus imaging system for imaging the eye fundus, said eye fundus imaging system guiding an imaging light beam from the eye fundus illuminated by said eye fundus illuminating system to the second optical path through said objective lens and said light beam separating element, wherein said imaging system comprises a movable mirror for opening the second optical path when said imaging system executes imaging, and for blocking and deflecting the second optical path when said imaging system does not execute imaging;

an eye refraction measuring system for projecting eye refraction measuring light to the fundus of an eye to be examined, and for measuring refractive information of an eye to be examined by detecting eye refraction measuring light reflected from the eye fundus; and an optical path dividing member, arranged between said objective lens and said light beam separating element for dividing an optical path of said eye refraction measuring system and an optical path of said eye fundus illuminating system and said eye fundus imaging system.

10. An ophthalmic apparatus comprising:

an objective lens arranged in a position opposite to an eye to be examined;

a light beam separating element, located at a position conjugate with the pupil of an eye to be examined, for separating a first optical path and a second optical path from the eye to be examined;

an eye fundus illuminating system for illuminating the fundus of an eye to be examined from the first optical path through said light beam separating element and said objective lens;

an eye fundus imaging system for imaging the eye fundus, said eye fundus imaging system guiding an imaging light beam from the eye fundus illuminated by said eye fundus illuminating system to the second optical path through said objective lens and said light beam separating element;

an eye refraction measuring system for projecting eye refraction measuring light to the fundus of an eye to be examined, and for measuring refractive information of an eye to be examined by detecting eye refraction measuring light reflected from the eye fundus;

an optical path dividing member comprising a movable mirror, arranged between said objective lens and said light beam separating element for dividing an optical path of said eye refraction measuring system and an optical path of said eye fundus illuminating system and said eye fundus imaging system.

* * * * *

UNITED STATES PATENT AND TRADEMARK OFFICE
CERTIFICATE OF CORRECTION

PATENT NO. : 5,420,650
DATED : May 30, 1995
INVENTOR(S) : YOSHIMI KOHAYAKAWA

It is certified that error appears in the above-indentified patent and that said Letters Patent is hereby corrected as shown below:

ON THE COVER PAGE

[54] Title

Line 3, "AND" should read --AND AN--.

COLUMN 1

Line 3, "AND" should read --AND AN--.

COLUMN 8

Line 22, "fundus;" should read --fundus; and--.

Signed and Sealed this

Tenth Day of October, 1995

BRUCE LEHMAN

Attest:

Attesting Officer

Commissioner of Patents and Trademarks